US00PP17152P2

(12) United States Plant Patent
Korlipara

(10) Patent No.: US PP17,152 P2
(45) Date of Patent: Oct. 10, 2006

(54) ***VERBASCUM* PLANT NAMED 'SIERRA SUNSET'**

(50) Latin Name: ***Verbascum* hybrid *((V. phoeniceum×dumulosum)×V.* sp.**
Varietal Denomination: Sierra Sunset

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 10 days.

(21) Appl. No.: 11/154,433

(22) Filed: Jun. 15, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct *Verbascum* plant characterized by numerous mango colored flowers on numerous short, upright flowering stems, a compact habit, and excellent vigor.

1 Drawing Sheet

Botanical denomination: *Verbascum* hybrid ((*V. phoeniceum×dumulosum*)×*V.* sp. 'Electric Yellow').

Variety designation: 'Sierra Sunset'.

Cross reference to: co-pending application for *Verbascum* 'Sunshine Spires' (U.S. Plant patent application Ser. No. 11/155,039).

The present invention relates to a new and distinct cultivar of *Verbascum* hybrid, and given the cultivar name 'Sierra Sunset'. *Verbascum* is in the family Scrophulariaceae.

This new cultivar originated from a cross between *Verbascum* 'Jackie' (an unpatented plant) as the seed parent and *Verbascum* sp. 'Electric Yellow' (an unpatented plant) as the pollen parent. *Verbascum* 'Jackie' is a cross between *Verbascum phoeniceum* and *Verbascum dumulosum.*

This new *Verbascum* hybrid is unique in its combination of bright mango colored flowers and its *Verbascum* 'Jackie'-like compact habit and short, multiple flowering stems.

This plant is characterized by the following:

1. Large mango colored flowers.
2. Numerous upright, branching flowering stems.
3. Compact habit.
4. Short flowering stems.
5. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the whole plant of a one year old *Verbascum* 'Sierra Sunset' grown in the trial field in bloom in late spring.

DETAILED PLANT DESCRIPTION

The following is a detailed description of the new *Verbascum* selection based on observations of one-year-old specimens grown in the ground in full sun under typical outdoor conditions Canby is Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:

*Type.*—Herbaceous perennial.
*Form.*—Clumping basal rosette.
*Hardiness.*—U.S.D.A. Hardiness Zones 6–9.
*Size.*—15 cm tall and 28 cm wide, not including inflorescence.
*Vigor.*—Excellent.
*Roots.*—With one main tap root, and many fibrous lateral branches, White 155A.
*Stem.*—Much congested, 1 cm deep and wide with no space between internodes.

Leaf:

*Type.*—Simple.
*Arrangement.*—Basal.
*Shape.*—Ovate.
*Blade size.*—Grows to 12 cm long and 7 cm wide.
*Venation.*—Pinnate.
*Margins.*—Irregularly crenate overall.
*Apex.*—Acute.
*Base.*—Cuneate.
*Texture.*—Leathery.
*Surface.*—Sparsely stellate pubescent.
*Petiole.*—Length — 3 cm. Width — Grows to 7 mm. Surface — Sparsely stellate pubescent. Color — Yellow Green 145C.
*Leaf color.*—Topside — Medium green. Green 147B with lighter main vein, Yellow Green 145C. Bottom side — Yellow Green 147B.

Inflorescence:

*Type.*—Panicle.

*Total panicle size.*—11 cm wide and 35 cm high (where flowers are).

*Number of panicles per plant in first flush.*—5.

*Cauline leaves.*—5 to 7 in number, 3 to 16.5 cm long and 1.5 to 7.5 cm wide.

*Flower number.*—Count of 70 flowers on one panicle.

*Peduncle.*—Height — 45 to 55 cm. Diameter — 6 mm near base. Surface — Stellate and glandular pubescent. Color — Yellow Green 144B.

*Pedicel.*—Length — 2 to 6 mm. Surface — Stellate and glandular pubescent. Color — Yellow Green 144D.

*Bloom time.*—May to August in Canby, Oreg.

Flower bud:

*Size.*—12 mm wide and 7 mm deep.

*Description.*—Pentagonal cushion.

*Surface.*—Stellate and glandular pubescent.

*Color.*—Orange brown, Greyed Orange 173A.

Flower:

*Type.*—Perfect. Complete. Irregular.

*Shape.*—Rotate, irregular, short tubular.

*Size.*—5 cm wide and 1.6 cm deep including stamens.

*Color.*—Top two petals are a deep mango color, between Orange 26C and Greyed Orange 163A with a darker edge, Greyed Orange 173A. The lower three petals are the mango color described above with a lighter gold in the center, Yellow Orange 20A to Yellow Orange 14C and lightening to Greyed Orange 163C. The center of the corolla is eyed purple, Greyed Purple 187B.

*Corolla.*—Petal number — 5. Description — Lobe margins entire, undulate, apex obtuse. Size — 5 cm wide and 1 cm deep. Surface — Backs stellate and glandular pubescent, front glabrous.

*Calyx.*—Sepal number — 5. Size — 15 mm wide and 10 mm deep. Surface — Stellate and glandular pubescent on both sides. Color — Yellow Green 144A.

*Stamens.*—Number — 5. Filaments — 8 mm long, Orange 24A at base and heavily bearded Red Purple 71A topped with Yellow 11C on upper three stamens. Anthers — Kidney shaped. Orange 24A. Pollen — Orange 24A.

*Style.*—14 mm long, Yellow Green 144A at tip to 144D at base.

*Stigma.*—Yellow Green 144A.

*Fragrance.*—None.

Fertility: Sterile, no fruit or seed produced.

Disease and pests: *Verbascum* are susceptible to fungal leaf spots and root rots. They need good drainage. Caterpillars may be a problem.

COMPARISONS

This new cultivar is very similar in growth habit and flowering habit to *Verbascum* 'Jackie' (unpatented). The greatest difference is the flower color. *V.* 'Jackie' is described as having copper colored buds, which open to pale peach colored flowers and lavender stamens. The new cultivar has red brown buds that open to mango colored flowers. *Verbascum* 'Sierra Sunset' the same good qualities of numerous flowering stems, short flowering stems, and compact habit of *Verbascum* 'Jackie'.

Compared to *Verbascum* 'Honey Dijon' (U.S. patent application Ser. No. 11/153,519), *Verbascum* 'Sunshine Spires' has bright yellow flowers rather than gold flowers, and has taller flowering stems.

I claim:

1. A new and distinct *Verbascum* plant characterized as herein illustrated and described.

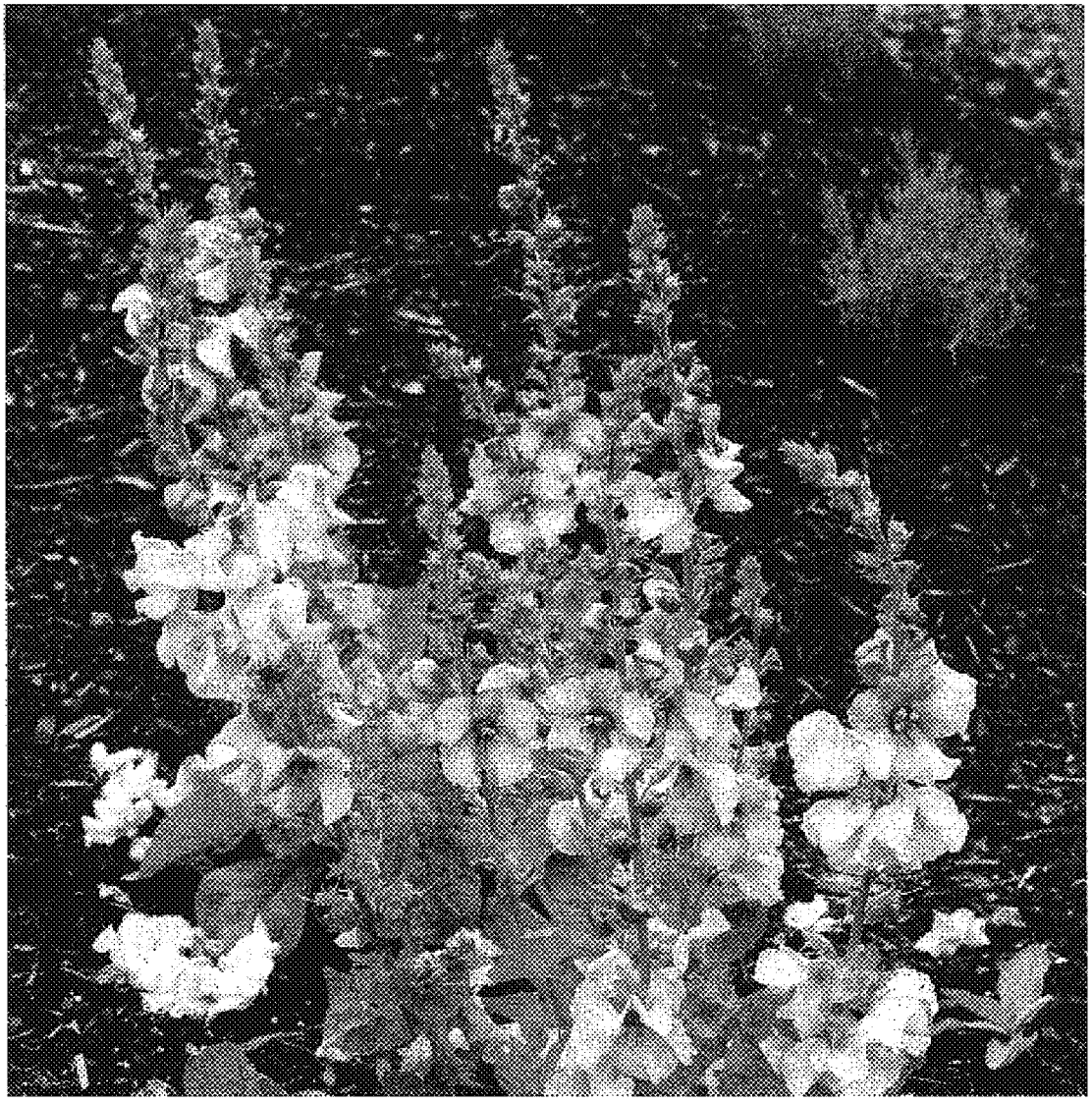

* * * * *